(12) United States Patent
Igarashi et al.

(10) Patent No.: US 8,278,615 B2
(45) Date of Patent: Oct. 2, 2012

(54) IMAGING SYSTEM HAVING A VARIABLE OPTICAL TRANSMISSION TIMING

(75) Inventors: Makoto Igarashi, Hachioji (JP); Kazuhiro Gono, Sagamihara (JM)

(73) Assignee: Olympus Medical Systems Corp., Tokyo (JP)

( * ) Notice: Subject to any disclaimer, the term of this patent is extended or adjusted under 35 U.S.C. 154(b) by 418 days.

(21) Appl. No.: 12/550,828

(22) Filed: Aug. 31, 2009

(65) Prior Publication Data

US 2010/0051789 A1    Mar. 4, 2010

(30) Foreign Application Priority Data

Sep. 4, 2008 (JP) .................................. 2008-227141

(51) Int. Cl.
*H01J 3/14* (2006.01)
(52) U.S. Cl. ........................................................ 250/216
(58) Field of Classification Search .................. 250/216, 250/225
See application file for complete search history.

(56) References Cited

U.S. PATENT DOCUMENTS

| | | | | |
|---|---|---|---|---|
| 5,001,556 A | * | 3/1991 | Nakamura et al. ............... | 348/70 |
| 5,847,394 A | * | 12/1998 | Alfano et al. ............... | 250/341.8 |
| 7,804,585 B2 | * | 9/2010 | Tropf .............................. | 356/3.1 |
| 2006/0147176 A1 | * | 7/2006 | Takamatsu et al. ........... | 385/147 |

FOREIGN PATENT DOCUMENTS

| | | |
|---|---|---|
| JP | 2005-087468 | 4/2005 |
| JP | 2006-200943 | 8/2006 |
| WO | WO 2005/027739 A1 | 3/2005 |
| WO | WO 2007/084915 A2 | 7/2007 |
| WO | WO 2007079805 A1 * | 7/2007 |

OTHER PUBLICATIONS

Extended European Search Report dated Feb. 3, 2010.
Bernet, et al., "Quantitative imaging of complex samples by spiral phase contrast microscopy", Optics Express, Optical Society of America, Washington DC, vol. 14, No. 9, May 1, 2006, pp. 3792-3805, XP002506161.

* cited by examiner

*Primary Examiner* — Thanh Luu
(74) *Attorney, Agent, or Firm* — Scully, Scott, Murphy & Presser, P.C.

(57) ABSTRACT

An imaging system according to the present invention includes: a light source unit which emits illuminating light to illuminate an object; an illuminating-light transmitting unit which transmits the illuminating light; a timing adjustment unit which, being placed between the illuminating-light transmitting unit and the object, varies timing with which rays contained in the illuminating light which has passed through the illuminating-light transmitting unit reach a surface of the object; a reflected-light incidence unit upon which reflected light coming from the surface of the object is incident; a light detection unit which temporally breaks down the reflected light incident upon the reflected-light incidence unit, converts the reflected light into an electrical signal, and outputs the electrical signal in sequence; and a signal processing unit which converts the electrical signal outputted in sequence by the light detection unit into pixel information about an optical image on the surface of the object.

5 Claims, 5 Drawing Sheets

IMAGING SYSTEM HAVING A VARIABLE OPTICAL TRANSMISSION TIMING

This application claims benefit of Japanese Application No. 2008-227141 filed in Japan on Sep. 4, 2008, the contents of which are incorporated by this reference.

BACKGROUND OF THE INVENTION

1. Field of the Invention

The present invention relates to an imaging system and, in particular, to an imaging system which allows a condition on a surface of an object to be observed by scanning the surface of the object with light.

2. Description of the Related Art

A technique for acquiring information about a surface of an object by scanning the surface of the object with light has been proposed in recent years. An example of such a technique is described in Japanese Patent Application Laid-Open Publication No. 2005-87468.

The technique disclosed in Japanese Patent Application Laid-Open Publication No. 2005-87468 involves emitting pulsed light repeatedly to an object, taking out a signal which depends on a delay time which occurs according to the time of flight required for reflected light of the pulsed light to reach a light-receiving surface of a sensor, and thereby acquiring a two-dimensional distribution of distance to the object.

SUMMARY OF THE INVENTION

The present invention provides an imaging system including: a light source unit which emits illuminating light to illuminate an object; an illuminating-light transmitting unit which transmits the illuminating light; a timing adjustment unit which, being placed between the illuminating-light transmitting unit and the object, varies timing with which rays contained in the illuminating light reach a surface of the object; a reflected-light incidence unit upon which reflected light coming from the surface of the object is incident; a light detection unit which temporally breaks down the reflected light incident upon the reflected-light incidence unit, converts the reflected light into an electrical signal, and outputs the electrical signal in sequence; and a signal processing unit which converts the electrical signal outputted in sequence by the light detection unit into pixel information about an optical image on the surface of the object.

DETAILED DESCRIPTION OF THE PREFERRED EMBODIMENTS

Embodiments of the present invention will be described below with reference to the drawings.

(First Embodiment)

Figure 1:
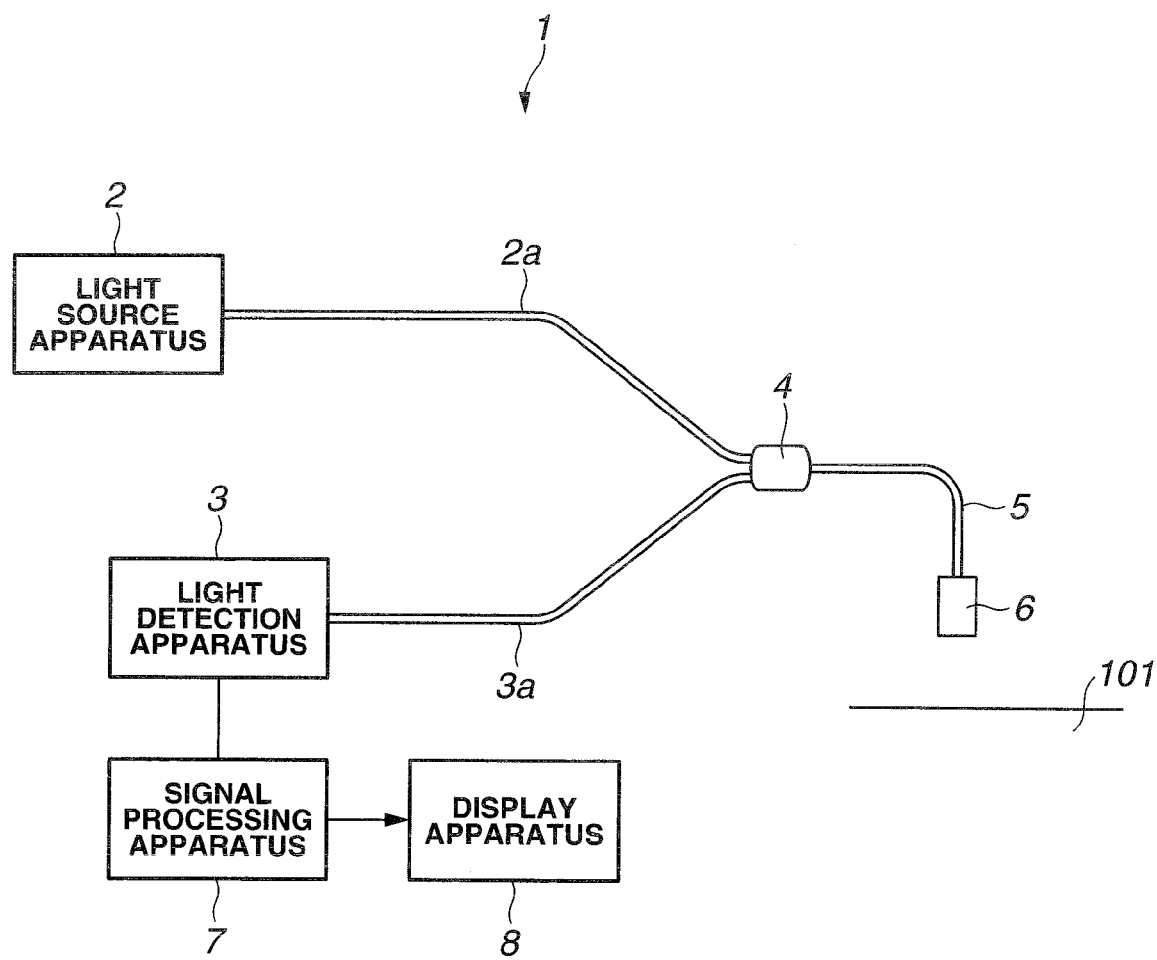
FIG. 1 is a diagram showing a configuration of principal part of an imaging system according to a first embodiment of the present invention.
Figure 2:
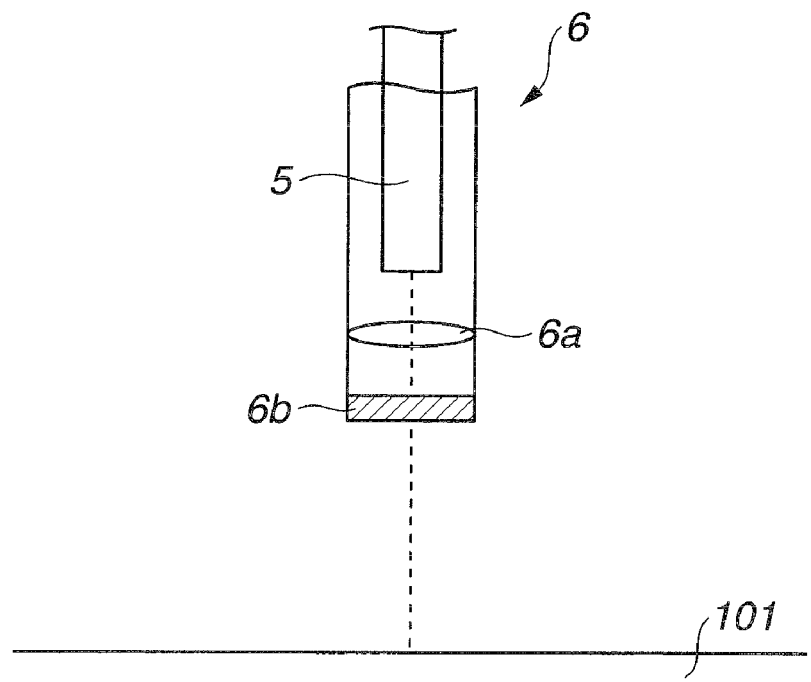
FIG. 2 is a diagram showing an exemplary configuration of a probe attached to the imaging system shown in FIG. 1.
Figure 3:
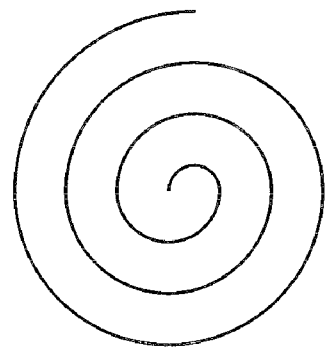
FIG. 3 is a diagram showing an example of a spiral pattern used in forming an optical Fourier mask.
Figure 4:
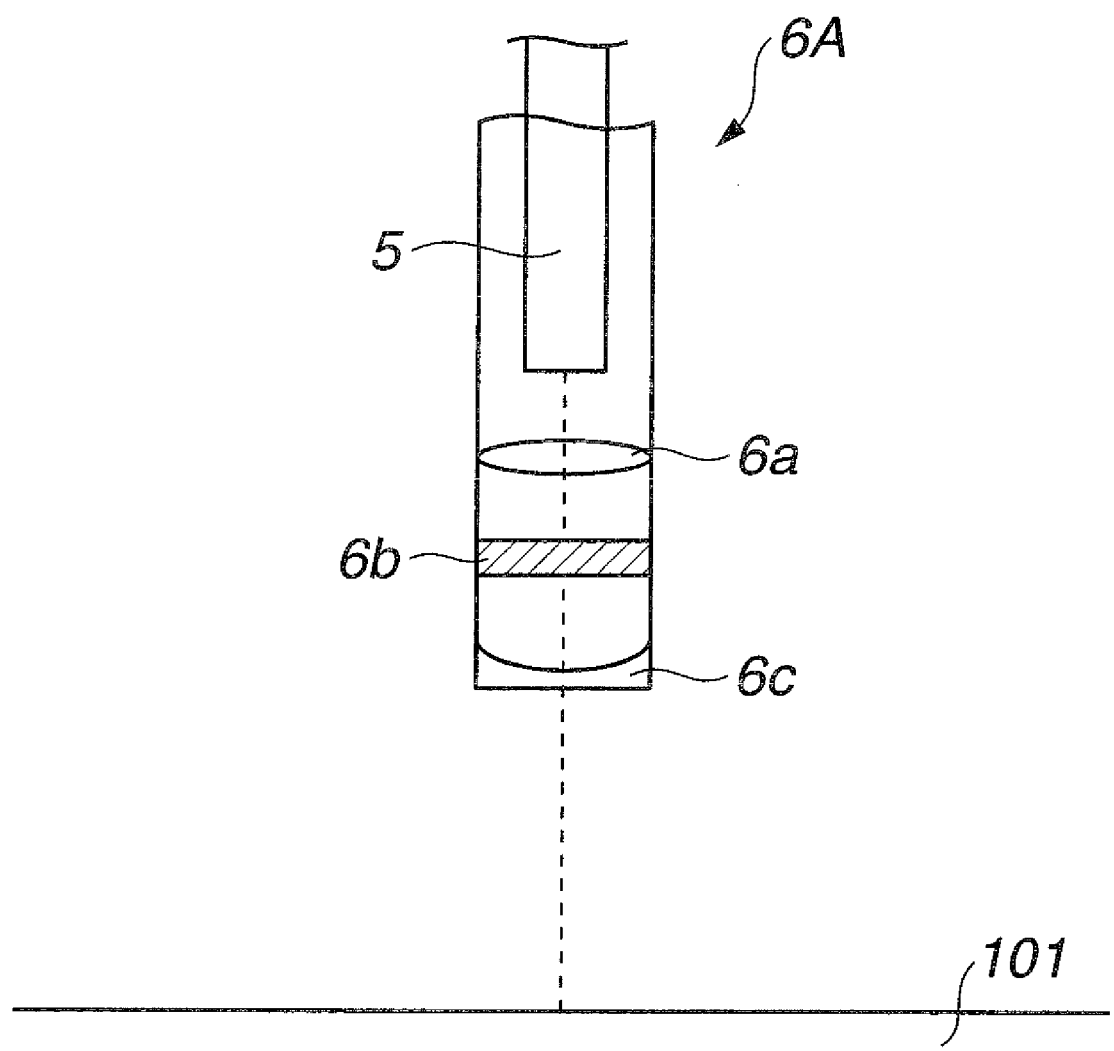
FIG. 4 is a diagram showing an exemplary configuration of a probe attached to the imaging system shown in FIG. 1, where the exemplary configuration is different from the one shown in FIG. 2.

FIGS. 1 to 4 concern a first embodiment of the present invention. FIG. 1 is a diagram showing a configuration of principal part of an imaging system according to the first embodiment of the present invention. FIG. 2 is a diagram showing an exemplary configuration of a probe attached to the imaging system shown in FIG. 1. FIG. 3 is a diagram showing an example of a spiral pattern used in forming an optical Fourier mask. FIG. 4 is a diagram showing an exemplary configuration of a probe attached to the imaging system shown in FIG. 1, where the exemplary configuration is different from the one shown in FIG. 2.

As shown in FIG. 1, an imaging system 1 includes a light source apparatus 2, illuminating-light guiding member 2a, light detection apparatus 3, reflected-light guiding member 3a, optical directional coupler 4, transmit/receive optical fiber 5, probe 6, signal processing apparatus 7, and display apparatus 8, where the light source apparatus 2 serves as a light source unit.

The light source apparatus 2 emits illuminating light to illuminate an object 101 such as living tissue. Also, the light source apparatus 2 is configured to be able to emit pulsed light or continuous light as the illuminating light. Alternatively, the light source apparatus 2 may be configured to emit light in a predetermined band as the illuminating light. Also, the light source apparatus 2 may be configured to be able to switch the type of illuminating light according to imaging mode, emitting white light when the object 101 is observed using full color images and emitting band-limited light when the object 101 is observed using spectral images.

The optical directional coupler 4 is configured to emit the light received from the illuminating-light guiding member 2a to the transmit/receive optical fiber 5 and emit the light received from the transmit/receive optical fiber 5 to the reflected-light guiding member 3a. Consequently, the illuminating light from the light source apparatus 2 is transmitted by the illuminating-light guiding member 2a, optical directional coupler 4, and transmit/receive optical fiber 5, and is then incident on the probe 6. That is, an illuminating-light transmitting unit of the imaging system 1 is made up of the illuminating-light guiding member 2a, optical directional coupler 4, and transmit/receive optical fiber 5.

As shown in FIG. 2, the probe 6 includes an end portion of the transmit/receive optical fiber 5, a collimating lens 6a, and an optical Fourier mask 6b, which are arranged in this order from a proximal side to a distal side. That is, the optical Fourier mask 6b of the imaging system 1 is installed between the end portion of the transmit/receive optical fiber 5 and the object 101.

The collimating lens 6a emits parallel light to the optical Fourier mask 6b by receiving light from the end portion of the transmit/receive optical fiber 5 as well as collects and focuses light from the optical Fourier mask 6b onto the end portion of the transmit/receive optical fiber 5.

The optical Fourier mask 6b, which functions as a timing adjustment unit, causes the illuminating light passing through the collimating lens 6a to be emitted to the object 101 as a light with a spiral pattern, for example, as shown in FIG. 3. It is assumed that all points on the spiral pattern are set at different distances from a center of the spiral pattern.

Consequently, the illuminating light transmitted to the probe 6 is emitted to the object 101 through the collimating lens 6a and optical Fourier mask 6b. Then, after being reflected by a surface of the object 101, the illuminating light is incident on the probe 6 as a reflected light. After passing through the optical Fourier mask 6b, collimating lens 6a, transmit/receive optical fiber 5, optical directional coupler 4, and reflected-light guiding member 3a in sequence, the reflected light is incident on the light detection apparatus 3. Incidentally, it is assumed that a reflected-light incidence unit of the imaging system 1 is embodied by (the end portion of) the transmit/receive optical fiber 5 placed in the probe 6.

The light detection apparatus 3 serving as a light detection unit receives light emitted from the reflected-light guiding member 3a, temporally breaks down the light, converts the light into an electrical signal, and outputs the electrical signal in sequence to the signal processing apparatus 7. To implement this function, the light detection apparatus 3 includes, for example, a point detector and a sensor such as a CCD or CMOS.

The signal processing apparatus 7 serving as a signal processing unit converts the electrical signal outputted in sequence by the light detection apparatus 3 into pixel information about an optical image of the object 101 and accumulates the pixel information. Upon detecting that one screen of the pixel information has been accumulated, the signal processing apparatus 7 outputs the one screen of pixel information as an image signal to the display apparatus 8. Consequently, the display apparatus 8 displays images of the object 101 for observation according to the image signal.

Next, operation of the imaging system 1 will be described.

First, a user places a distal end face of the probe 6 approximately in parallel to the surface of the object 101 by moving the probe 6. Consequently, the illuminating light emitted from the probe 6 is emitted approximately vertically to the surface of the object 101.

The user turns on power to various parts of the imaging system 1 to emit pulsed or continuous illuminating light from the light source apparatus 2.

The illuminating light emitted from the light source apparatus 2 passes through the illuminating-light guiding member 2a, optical directional coupler 4, transmit/receive optical fiber 5, and collimating lens 6a, and then the optical Fourier mask 6b.

The time required to reach the surface of the object 101 (and thus, timing of arrival at the surface of the object 101) varies among rays contained in the illuminating light which has passed through the optical Fourier mask 6b. That is, the rays contained in the illuminating light emitted from a distal end portion of the probe 6 are reflected from the surface of the object 101 with different reflection timings.

Rays contained in the light reflected from the surface of the object 101 are incident upon the probe 6 with different timings. Then, after passing through the optical directional coupler 4 and reflected-light guiding member 3a in sequence, the rays are incident upon the light detection apparatus 3.

The light detection apparatus 3 receives and temporally breaks down the light incident upon the light detection apparatus 3, converts the light into an electrical signal, and outputs the electrical signal in sequence to the signal processing apparatus 7.

The signal processing apparatus 7 converts the electrical signal outputted in sequence by the light detection apparatus 3 into pixel information about an optical image of the object 101 and accumulates the pixel information. There is no temporal overlap among multiple pieces of pixel information generated and accumulated by the signal processing apparatus 7. Thus, the signal processing apparatus 7 simultaneously generates and accumulates the pixel information by uniquely identifying the pixel information at any location on a plane (surface) of the object 101.

Upon detecting that one screen of pixel information has been accumulated, the signal processing apparatus 7 outputs the one screen of pixel information as an image signal to the display apparatus 8. Consequently, the display apparatus 8 displays an image of the object 101 in which planar orientation can be identified sufficiently.

As described above, by using the optical Fourier mask 6b which generates a light with a spiral pattern, the imaging system 1 according to the present embodiment ensures that the rays contained in the illuminating light emitted from the distal end portion of the probe 6 will be reflected from the surface of the object 101 with different reflection timings. Consequently, the imaging system 1 according to the present embodiment can acquire information about the surface of an object accurately when scanning the surface of the object with light.

Incidentally, the imaging system 1 according to the present embodiment is not limited to a configuration in which the illuminating-light guiding member 2a and reflected-light guiding member 3a are installed separately, and may have a configuration in which the illuminating-light guiding member 2a and reflected-light guiding member 3a are formed integrally.

Also, the imaging system 1 according to the present embodiment is not limited to a configuration in which the collimating lens 6a and optical Fourier mask 6b are provided as separate optical members, and, for example, may have an optical member which combines the functions of the collimating lens 6a and optical Fourier mask 6b.

Furthermore, the imaging system 1 according to the present embodiment may be configured to transmit and receive light, for example, by vibrating the end portion of the transmit/receive optical fiber 5 placed in the probe 6.

Besides, the imaging system 1 according to the present embodiment may have a probe 6A shown in FIG. 4 instead of the probe 6 shown in FIG. 2

As shown in FIG. 4, the probe 6A includes an end portion of the transmit/receive optical fiber 5, a collimating lens 6a, an optical Fourier mask 6b, and an objective optical system 6c, which are arranged in this order from the proximal side to the distal side.

The objective optical system 6c is configured to be able to extend an emission range of the illuminating light passed through the optical Fourier mask 6b and allows the light reflected from the surface of the object 101 to pass by maintaining its course.

The use of the probe 6A with this configuration makes it possible to acquire information from a wider area on the surface of the object 101.

With the imaging system 1 according to the present embodiment, a shutter may be installed in front of a light-receiving unit of the light detection apparatus 3 and the timing of emission of the illuminating light from the light source apparatus 2 may be synchronized with the timing of opening and closing of the shutter.

(Second Embodiment)

Figure 5:
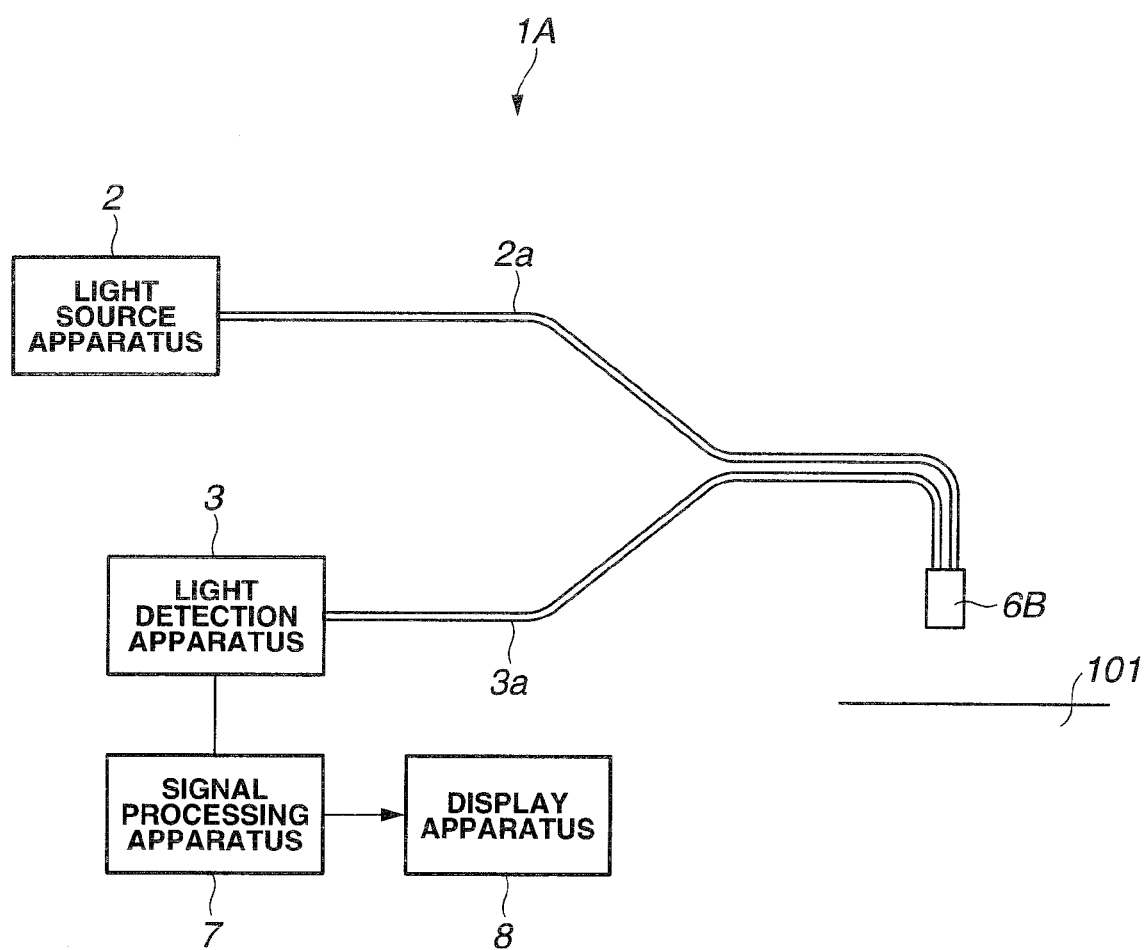
FIG. 5 is a diagram showing a configuration of principal part of an imaging system according to a second embodiment of the present invention.
Figure 6:
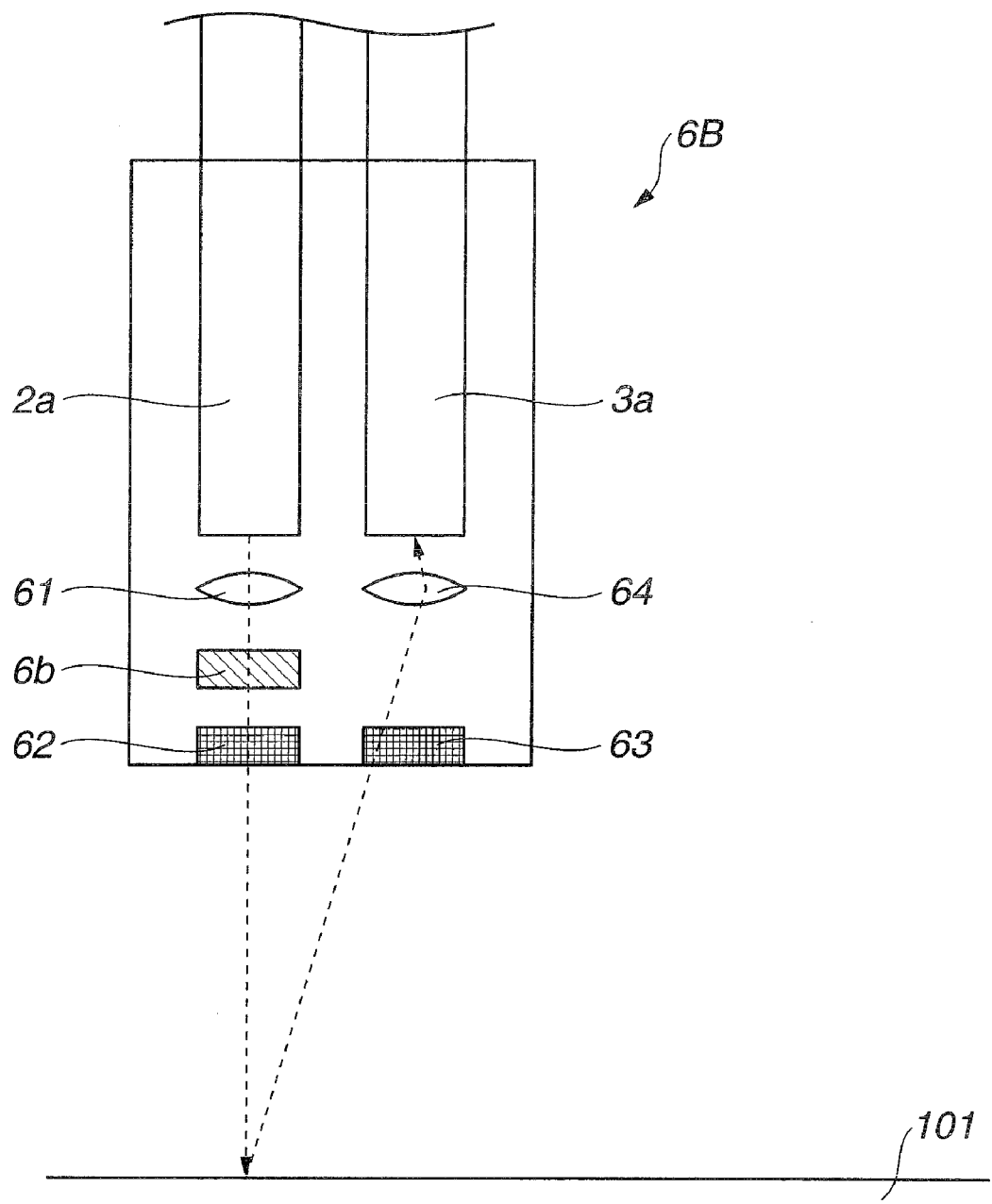
FIG. 6 is a diagram showing an exemplary configuration of a probe attached to the imaging system shown in FIG. 5.

FIGS. 5 and 6 concern a second embodiment of the present invention. FIG. 5 is a diagram showing a configuration of principal part of an imaging system according to the second embodiment of the present invention. FIG. 6 is a diagram showing an exemplary configuration of a probe attached to the imaging system shown in FIG. 5.

Detailed description of components similar to those of the first embodiment will be omitted below. An imaging system according to the present embodiment has a configuration similar to the configuration of the imaging system 1 according to the first embodiment. Thus, parts different from the imaging system 1 according to the first embodiment will mainly be described in the second embodiment.

As shown in FIG. 5, an imaging system 1A includes a light source apparatus 2, illuminating-light guiding member 2a, light detection apparatus 3, reflected-light guiding member 3a, probe 6B, signal processing apparatus 7, and display apparatus 8.

As shown in FIG. 6, the probe 6B includes an end portion of the illuminating-light guiding member 2a, a collimating lens 61, an optical Fourier mask 6b, and a polarizer 62, which are arranged in order from the proximal side to the distal side. The illuminating light emitted from the light source apparatus 2 is emitted to the surface of the object 101 after passing through the above-described components in order. That is, an illuminating-light transmitting unit of the imaging system 1A is made up of an illuminating-light guiding member 2a. The optical Fourier mask 6b of the imaging system 1A is installed between an end portion of the illuminating-light guiding member 2a and the object 101. Furthermore, the polarizer 62 of the imaging system 1A is installed between the optical Fourier mask 6b and object 101.

Also, as shown in FIG. 6, the probe 6B includes an analyzer 63, a collimating lens 64, and an end portion of the reflected-light guiding member 3a, which are arranged in this order from the proximal side to the distal side. The light reflected from the surface of the object 101 is finally transmitted to the light detection apparatus 3 after passing through the above-described components in order. Incidentally, a reflected-light incidence unit of the imaging system 1A is embodied by (the end portion of) the reflected-light guiding member 3a placed in the probe 6B. Also, the analyzer 63 of the imaging system 1A is installed between the object 101 and the end portion of reflected-light guiding member 3a.

The collimating lens 61 emits parallel light to the optical Fourier mask 6b by receiving light from the end portion of the illuminating-light guiding member 2a.

The polarizer 62 emits the illuminating light passed through the optical Fourier mask 6b to the surface of the object 101 by aligning the illuminating light along a first polarizing direction.

With this configuration, rays contained in the illuminating light emitted from the light source apparatus 2 have a spiral pattern and are emitted to the surface of the object 101 by being uniformly polarized along a first polarizing direction.

The analyzer 63 emits the light reflected by the object 101 to the collimating lens 64 by aligning the light along a second polarizing direction orthogonal to the first polarizing direction. Consequently, the analyzer 63 removes a component reflected by a depth (inner part) of the object 101 from the light reflected by the object 101 and thereby extracts only a component reflected by the surface of the object 101.

The collimating lens 64 collects and focuses the light passing through the analyzer 63 on the end portion of the reflected-light guiding member 3a.

This configuration causes the rays contained in the light reflected by the object 101 to have different reflecting timings: the rays are incident upon the end portion of the reflected-light guiding member 3a, being uniformly polarized along the second polarizing direction, and eventually transmitted to the light detection apparatus 3.

The light detection apparatus 3 receives and temporally breaks down the light incident upon the light detection apparatus 3, converts the light into an electrical signal, and outputs the electrical signal in sequence to the signal processing apparatus 7.

The signal processing apparatus 7 converts the electrical signal outputted in sequence by the light detection apparatus 3 into pixel information about an optical image of the object 101 and accumulates the pixel information. There is no temporal overlap among multiple pieces of pixel information generated and accumulated by the signal processing apparatus 7. Thus, the signal processing apparatus 7 simultaneously accumulates and generates the pixel information by uniquely identifying the pixel information at any location on a plane of the object 101.

Upon detecting that one screen of pixel information has been accumulated, the signal processing apparatus 7 outputs the one screen of pixel information as an image signal to the display apparatus 8. Consequently, the display apparatus 8 displays an image of the object 101, where the image allows planar orientation to be identified sufficiently, and the object 101 to be observed in detail.

As described above, the imaging system 1A according to the present embodiment can acquire information about the surface of an object more accurately when scanning the surface of the object with light.

The second polarizing direction of the analyzer 63 does not necessarily need to be orthogonal to the first polarizing direction of the polarizer 62 as long as the second polarizing direction is different from the first polarizing direction.

The present invention is not limited to the above embodiments and various changes and applications are possible within the spirit and scope of the present invention.

What is claimed is:

1. An imaging system, comprising:
   a light source unit which emits illuminating light to illuminate an object;
   an illuminating-light transmitting unit which transmits the illuminating light;
   a timing adjustment unit which, being placed between the illuminating-light transmitting unit and the object, individually varies a transmission timing of rays contained in the illuminating light with respect to one another, causing the rays to reach a surface of the object at respectively different times;
   a reflected-light incidence unit upon which reflected light coming from the surface of the object is incident;
   a light detection unit which temporally breaks down the reflected light incident upon the reflected-light incidence unit, converts the reflected light into an electrical signal, and outputs the electrical signal in sequence; and
   a signal processing unit which converts the electrical signal outputted in sequence by the light detection unit into pixel information about an optical image on the surface of the object,
   wherein the timing adjustment unit emits the illuminating light which has passed through the illuminating-light transmitting unit to the object as a light with a spiral pattern.

2. The imaging system according to claim 1, wherein the timing adjustment unit is configured as an optical Fourier mask which generates the light with the spiral pattern.

3. The imaging system according to claim 1, wherein the light source unit emits pulsed light as the illuminating light.

4. The imaging system according to claim 1, wherein the light source unit emits continuous light as the illuminating light.

5. The imaging system according to claim 1, further comprising:

a polarizer which, being installed between the timing adjustment unit and the object, aligns the illuminating light which has passed through the timing adjustment unit along a first polarizing direction; and an analyzer which, being installed between the object and the reflected-light incidence unit, aligns the light reflected by the surface of the object along a second polarizing direction orthogonal to the first polarizing direction.

\* \* \* \* \*

UNITED STATES PATENT AND TRADEMARK OFFICE
CERTIFICATE OF CORRECTION

PATENT NO. : 8,278,615 B2
APPLICATION NO. : 12/550828
DATED : October 2, 2012
INVENTOR(S) : Makoto Igarashi et al.

It is certified that error appears in the above-identified patent and that said Letters Patent is hereby corrected as shown below:

On the Title Page:

Item (75) should read:

(75)    Inventors: Makoto Igarashi, Hachioji (JP)
                    Kazuhiro Gono, Sagamihara (JP)

Signed and Sealed this
Twenty-fifth Day of December, 2012

David J. Kappos
*Director of the United States Patent and Trademark Office*